United States Patent [19]

Smith et al.

[11] 4,308,030
[45] Dec. 29, 1981

[54] METHOD OF DETERMINATION OF ALKALINE EARTH METAL IONS IN CONCENTRATED ALKALI METAL CHLORIDE BRINES

[75] Inventors: Maurice R. Smith, Cleveland; Harvey B. Cochran, Englewood, both of Tenn.

[73] Assignee: Olin Corporation, New Haven, Conn.

[21] Appl. No.: 224,349

[22] Filed: Jan. 12, 1981

[51] Int. Cl.$^3$ .............................................. G01N 33/20
[52] U.S. Cl. .............................. 23/230 PC; 23/230 R; 204/98
[58] Field of Search .......... 23/230 R, 230 PC, 230 A; 204/98

[56] References Cited

U.S. PATENT DOCUMENTS 4,060,465 11/1977 Yokota et al.
4,176,022 11/1979 Darlington ............................ 204/98
4,202,743 5/1980 Oda et al. ............................... 204/98

*Primary Examiner*—Ronald Serwin
*Attorney, Agent, or Firm*—J. B. Haglind; D. F. Clements

[57] ABSTRACT

A method for determining low level concentrations of alkaline earth metals in a concentrated aqueous alkali metal chloride brine containing alkaline earth metal ions comprises heating a sample of the brine to a temperature sufficient to remove water and form anhydrous alkali metal chloride. The anhydrous alkali metal chloride is then further heated to a temperature range in which the alkali metal chloride undergoes a change. The anhydrous alkali metal chloride is then vaporized and the alkaline earth metals atomized and passed through an analyzer where the concentration of alkaline earth metals are determined.

Using the method of the present invention, alkaline earth metals such as calcium can be detected in concentrations as low as 1 part per billion, while magnesium can be detected in concentrations as low as 0.4 parts per billion.

12 Claims, No Drawings

METHOD OF DETERMINATION OF ALKALINE EARTH METAL IONS IN CONCENTRATED ALKALI METAL CHLORIDE BRINES

This invention relates to improvements in the determination of impurities in alkali metal chloride brines. More particularly, the invention concerns the determination of alkaline earth metal impurities in alkali metal chloride brines.

Aqueous solutions of alkali metal chlorides are used in the electrolytic production of chlorine and alkali metal hydroxides in electrolytic cells employing a diaphragm or membrane. It is well known that during electrolysis, the diaphragm or membrane is deleteriously affected by significant concentrations of alkaline earth metal ions such as calcium or magnesium ions being present in the chloride solutions. Brines suitable for electrolytic cells employing hydraulically permeable diaphragms contain a few parts per million of alkaline earth metals and can be obtained by the normal treatment processes in which sodium carbonate and sodium hydroxide are employed to precipitate excess calcium and magnesium present.

In electrolytic cells employing hydraulically impermeable membranes such as those composed of ion exchange resins, it is necessary to reduce the alkaline earth metal impurity levels to concentrations in the parts per billion range.

Suitable methods for purifying alkali metal chloride brines to obtain these low level concentrations of alkaline earth metal impurities include, for example, those of U.S. Pat. No. 4,176,022, issued Nov. 27, 1979, to W. B. Darlington; U.S. Pat. No. 4,060,465, issued Nov. 29, 1977, to N. Yokota et al; or U.S. Pat. No. 4,202,743, issued May 13, 1980, to Y. Oda et al.

To successfully employ these methods of purification, it is necessary to have methods of detection which can readily determine low level concentrations of alkaline earth metal ions.

It is an object of the present invention to provide a method for accurately determining low level concentrations of alkaline earth metals in concentrated aqueous alkali metal chloride brines.

Another object of the present invention is to provide a method for the rapid determination of low level concentrations of alkaline earth metals in concentrated aqueous alkali metal chloride brines.

These and other objects of the invention are accomplished in a method for determining low level concentrations of alkaline earth metals in a concentrated aqueous alkali metal chloride brine which comprises:

(a) heating a sample of the brine to a temperature sufficient to remove water and form anhydrous alkali metal chloride, (b) further heating the anhydrous alkali metal chloride to a temperature in the range of from about 180° to about 300° C. and maintaining the temperature for a predetermined period, (c) vaporizing the anhydrous alkali metal chloride at a temperature above about 1300° C., (d) atomizing the alkaline earth metals at a temperature above about 2600° C., and (e) determining the concentration of the atomized alkaline earth metals.

More in detail, the method of the present invention may be employed with any concentrated alkali metal chloride brines such as those of sodium chloride, potassium chloride, or lithium chloride. For example, where sodium chloride brine is employed, suitable concentrations are those in the range of from about 200 to about 320 grams per liter of NaCl. These brines are purified by known techniques to reduce the concentrations of alkaline earth metals. Typically, purified brines have calcium concentrations of less than 100 parts per billion, for example, in the range of about 5 to about 100 parts per billion while magnesium concentrations are less than 50 parts per billion, for example, in the range of from about 1 to about 50 parts per billion. Other impurities may be present in the purified concentrated brines including, for example, sodium sulfate and sodium carbonate.

The method of the present invention can be employed with any analyzer apparatus which determines the concentration of alkaline earth metals in their atomized form. Suitable analyzers include flame or flameless atomic absorption spectrophotometers, atomic emission spectrophotometers, and spark source mass spectrometers.

In order to simplify the disclosure, the method of the present invention will be described in terms of calcium and magnesium determination in concentrated sodium chloride brines employing a graphite furnace in which the brine sample is atomized in the light path of an atomic absorption spectrophotometer analyzer. Samples of sodium chloride brines having low level concentrations of calcium and magnesium are supplied to the graphite furnace and are initially heated to a temperature suitable for vaporizing the water present. For example, concentrated sodium chloride brines are suitably heated to a temperature in the range of from about 120° to about 130° C. Any suitable time period (ramp) may be used in the initial heating, for example, from about 20 to about 30 seconds. At this temperature, the brine sample is held long enough to remove water present and form anhydrous sodium chloride containing calcium and magnesium. The anhydrous sodium chloride is further heated to a temperature in the range of from about 180° to about 300° C. over a period (ramp) of about 20 to about 40 seconds. The anhydrous sodium chloride is maintained at this temperature for a minimum period of about 10 seconds during which the sodium chloride appears to undergo a change. It is not known exactly what physical or chemical changes the anhydrous sodium chloride undergoes during this period. Under visual observation, the anhydrous sodium chloride appears to undergo an expansion and contraction. During this change, there is apparently no loss or removal of alkaline earth metal impurities. Employing controlled heating conditions during this change allows higher precision analysis in the analyzer with a lower standard deviation range than can be attained when the anhydrous sodium chloride is rapidly heated to the temperature at which it vaporizes. Rapid heating of the brine to the temperature at which sodium chloride vaporizes appears to result in a loss of calcium and magnesium.

The temperature of the anhydrous sodium chloride is now raised to the temperature at which NaCl vaporizes, i.e., a temperature above about 1300° C., for example, in the range of from about 1400° to about 1450° C. This temperature was maintained for a sufficient time to completely vaporize the NaCl, i.e., from about 20 to about 30 seconds. To atomize the alkaline earth metal ions, the temperature of the sample was raised to at least about 2600° C.

In a preferred embodiment, prior to atomizing calcium and magnesium, sodium chloride vapors are removed from the heating zone. Any suitable means of removing the vaporized sodium chloride may be employed including vacuum means or purging with an inert gas such as argon or nitrogen.

To insure homogeneity of the atomized sample in the light path of the atomic absorption spectrophotometer, an inert gas such as argon or nitrogen may be employed. Suitable gas flow rates during the atomization of the alkaline earth metal ions include those in the range of from about 30 to about 500, and preferably from about 100 to about 300 millimeters per minute.

Employing the novel method of the present invention, accurate determination of concentrations of alkaline earth metals such as calcium and magnesium in parts per billion or less can be attained in concentrated brine samples. The detection limit for calcium is on the order of 1 part per billion while the 95 percent confidence limit is on the order of ±5 parts per billion. Magnesium can be detected in concentrations as low as 0.4 parts per billion where the 95 percent confidence limit is ±0.7 parts per billion. The novel method permits the determination of alkaline earth metals in alkali metal chloride brines to be carried out in short time periods, for example, in from about 3 to about 5 minutes. In an electrolysis process, the method of the present invention permits the accurate analysis of alkaline earth metals in purified brine samples, for example, eluting from ion exchange columns, to be carried out rapidly. This novel method readily determines the "breakthrough" point of the resin in the column so that the brine stream can be quickly switched to an alternate column and avoid feeding brines with excessive amounts of calcium and magnesium to the electrolytic cells.

The method of the present invention assures high precision analysis of alkaline earth metals in brine as it minimizes or eliminates the loss of alkaline earth metals during the vaporization and atomization stages.

To further illustrate the novel method of the present invention, the following example is presented. All percentages are by weight unless otherwise specified.

EXAMPLE

Sodium chloride brine (300 grams per liter of NaCl), produced by dissolving rock salt, was treated with soda ash and sodium hydroxide and filtered to remove precipitated solids. The treated brine was then passed through two ion exchange columns operated in series before being fed to an electrolytic membrane cell. Calcium and magnesium ions contained as impurities in the brine were reduced to concentrations below 1 part per million during passage of the brine through the ion exchange resin. A sample of the purified brine passing from the second ion exchange column was taken and introduced into a graphite furnace (Perkin-Elmer HGA 500) for atomization. To remove the water present, the furnace was heated to 120° C. over a 20 second period (ramp). This temperature was held for about 10 seconds to completely vaporize the water and form anhydrous sodium chloride containing impurities including Ca and Mg. The anhydrous sodium chloride sample was further heated for about 30 seconds while visually observing the sample. At a temperature of about 190° C., the anhydrous sodium chloride appeared to undergo a change in which an expansion and contraction took place. During this change, the temperature was maintained at 190° C. for about 15 seconds. To vaporize NaCl, the sample was heated to 1450° C. over a period (ramp) of 60 seconds. This temperature was held for 30 seconds to completely vaporize NaCl. Vaporized NaCl was purged from the alkaline earth metal impurities by passing argon gas through the vaporization chamber at a rate of 300 mls per minute. To atomize Ca and Mg, the temperature of the furnace was rapidly increased (1 second ramp) to 2600° C. and held for 5 seconds. Argon gas flow was maintained through the uncoated graphite tube, at a rate of 100 ml/min. The graphite tube was positioned in the light path of an atomic absorption spectophotometer (Perkin-Elmer Model 560) for analysis. A concentration of calcium of 8 ppb (±4 ppb with a 95% confidence limit) was found while the magnesium concentration present was determined to be 3 ppb (±0.3 ppb with a 95% confidence limit). The analysis from the time of sample introduction into the graphite furnace to reading off the alkaline earth absorbents was found to be 3 minutes and 6 seconds.

What is claimed is:

1. A method for determining low level concentrations of alkaline earth metals in a concentrated aqueous alkali metal chloride brine which comprises:
   (a) heating a sample of said brine in a heating means to a temperature sufficient to remove water and form anhydrous alkali metal chloride,
   (b) further heating said anhydrous alkali metal chloride to a temperature in the range of from about 180° to about 300° C. and maintaining said temperature for a predetermined time period,
   (c) vaporizing said anhydrous alkali metal chloride at a temperature above about 1300° C.,
   (d) atomizing said alkaline earth metals at a temperature above about 2600° C., and
   (e) determining the concentration of said alkaline earth metal ions.

2. The method of claim 1 in which said alkali metal brine is sodium chloride or potassium chloride.

3. The method of claim 2 in which said alkaline earth metals are calcium and magnesium.

4. The method of claim 3 in which said analyzer is selected from the group consisting of atomic absorption spectrophotometers, atomic emission spectrophotometers, and spark source mass spectrometers.

5. The method of claim 4 in which said predetermined time period of step (b) is from about 20 to about 40 seconds.

6. The method of claim 5 in which said heating means is a graphite furnace.

7. The method of claim 1 or 6 in which, prior to step (d), said vaporized alkali metal chloride is removed.

8. The method of claim 7 in which said calcium is present in a concentration in the range of from about 1 to about 100 parts per billion.

9. The method of claim 8 in which said magnesium is present in a concentration of from about 0.4 to about 50 parts per billion.

10. The method of claim 9 in which said alkali metal chloride brine is sodium chloride in a concentration of from about 200 to about 320 grams per liter.

11. The method of claim 10 in which said analyzer is an atomic absorption spectrophotometer and said heating means is a graphite furnace.

12. The method of claim 11 in which said vaporized alkali metal chloride is removed by purging with an inert gas.

* * * * *